United States Patent
Welch et al.

(10) Patent No.: US 8,479,556 B2
(45) Date of Patent: Jul. 9, 2013

(54) I-BEAM WEAR ASSESSMENT TROLLEYS AND METHODS FOR USING THE SAME

(75) Inventors: Edward R. Welch, Georgetown, KY (US); Tomokazu Okuno, Toyota Aichi (JP); Tetsuya Yamaguchi, Nagoya Aichi (JP)

(73) Assignee: Toyota Motor Engineering & Manufacturing North America, Inc., Erlanger, NY (US)

( * ) Notice: Subject to any disclaimer, the term of this patent is extended or adjusted under 35 U.S.C. 154(b) by 273 days.

(21) Appl. No.: 12/981,866

(22) Filed: Dec. 30, 2010

(65) Prior Publication Data
US 2012/0167661 A1    Jul. 5, 2012

(51) Int. Cl.
*G01N 3/56* (2006.01)
*G01M 5/00* (2006.01)

(52) U.S. Cl.
CPC .......... *G01M 5/0025* (2013.01); *G01M 5/0033* (2013.01); *G01M 5/0075* (2013.01)
USPC ..................................................... 73/7; 73/8

(58) Field of Classification Search
USPC ................................... 33/287, 523.2; 73/8, 7
See application file for complete search history.

(56) References Cited

U.S. PATENT DOCUMENTS

| | | | |
|---|---|---|---|
| 2,030,354 A | 2/1936 | Czemba | |
| 2,765,068 A | 10/1956 | Daigle | |
| 3,500,549 A | 3/1970 | Smith | |
| 4,248,157 A * | 2/1981 | Evans | 105/154 |
| 4,288,855 A | 9/1981 | Panetti | |
| 4,495,635 A | 1/1985 | Dobbs | |
| 4,625,412 A * | 12/1986 | Bradshaw | 33/1 Q |
| 5,353,512 A | 10/1994 | Theurer et al. | |
| 5,490,590 A | 2/1996 | Courtney | |
| 5,563,392 A | 10/1996 | Brown et al. | |
| 5,773,714 A | 6/1998 | Shead | |
| 2002/0017140 A1 * | 2/2002 | Georgeson et al. | 73/618 |

FOREIGN PATENT DOCUMENTS

| | | | |
|---|---|---|---|
| JP | 2003207331 A | * | 7/2003 |
| JP | 2003344036 A | * | 12/2003 |
| JP | 2008249508 A | * | 10/2008 |

OTHER PUBLICATIONS

English Translation of JP 2003207331 A.*

* cited by examiner

*Primary Examiner* — Hezron E Williams
*Assistant Examiner* — Alexander Mercado
(74) *Attorney, Agent, or Firm* — Dinsmore & Shohl LLP

(57) ABSTRACT

I-beam wear assessment trolleys include a first sensor assembly including a first upper block, a first lower block, a first pressure sensor positioned between the first upper block and the first lower block, and at least one first biasing member positioned between the first pressure sensor and either the first upper block or the first lower block of the first sensor assembly, wherein the at least one first biasing member biases the first upper block and the first lower block of the first sensor assembly away from one another.

20 Claims, 6 Drawing Sheets

I-BEAM WEAR ASSESSMENT TROLLEYS AND METHODS FOR USING THE SAME

TECHNICAL FIELD

The present specification generally relates to I-beam rail guides and, more specifically, to apparatuses for assessing I-beam rail guide flange wear.

BACKGROUND

I-beams may be utilized as rail guides for transporting parts or equipment around assembly lines during a manufacturing process. In operation, carriers for transporting parts can connect to wheels that ride on the flanges on either side of the I-beam. Specifically, the wheels of the carrier may ride against the upper flange and/or lower flange. However, the wheels for the carriages wear the flanges of the I-beam such that the flanges become thin and lose their structural support. Therefore, I-beams used for rail guides are often inspected to determine the amount of wear on the flanges so that potentially dangerous portions may be repaired, such as by welding additional material support to the worn section, or replaced, such as by changing out a worn portion of an I-beam with a new portion of an I-beam. I-beam wear inspection is often conducted manually by measuring the thickness of the flanges along the length of the entire I-beam. However, this process requires significant time and expense and potentially requires that the assembly line be shut down as wear measurements are taken and sections of the I-beam are replaced.

Accordingly, a need exists for alternative methods and apparatus for I-beam wear assessment.

SUMMARY

In one embodiment, an I-beam wear assessment trolley includes a first sensor assembly including a first upper block, a first lower block, a first pressure sensor positioned between the first upper block and the first lower block, and at least one first biasing member positioned between the first pressure sensor and either the first upper block or the first lower block of the first sensor assembly, wherein the at least one first biasing member biases the first upper block and the first lower block of the first sensor assembly away from one another.

In another embodiment, an I-beam wear assessment trolley includes a first sensor assembly including a first upper block, a first lower block, a first pressure sensor positioned between the first upper block and the first lower block, and at least one first biasing member positioned between the first pressure sensor and either the first upper block or the first lower block of the first sensor assembly, wherein the at least one first biasing member biases the first upper block and the first lower block of the first sensor assembly away from one another, and a second sensor assembly removably coupled to the first sensor assembly with a coupling yoke, the second sensor assembly including a second upper block, a second lower block, second pressure sensor positioned between the second upper block and the second lower block, and at least one second biasing member positioned between the second pressure sensor and either the second upper block or the second lower block of the second sensor assembly, wherein the second biasing member biases the second upper block and the second lower block of the second sensor assembly away from one another. The I-beam wear assessment trolley can further include, a computer communicatively coupled to the first sensor assembly and the second sensor assembly, the computer including a processor and a memory with computer readable and executable instructions, wherein the processor executes the computer readable and executable instructions to receive a first wear signal from the first pressure sensor indicative of a first block height between the first upper block and the first lower block, receive a second wear signal from the second pressure sensor indicative of a second block height between the second upper block and the second lower block, and store the first wear signal and the second wear signal in the memory based on a position of the first sensor assembly and the second sensor assembly along a length of an I-beam.

In yet another embodiment, a method for assessing the wear of an I-beam is provided. The method includes positioning a first sensor assembly between an upper flange and a lower flange of the I-beam, the first sensor assembly comprising a first upper block, a first lower block, a first pressure sensor positioned between the first upper block and the first lower block, and at least one first biasing member positioned between the first upper block and the first lower block, wherein the at least one first biasing member biases the first upper block and the first lower block of the first sensor assembly away from one another, traversing the first sensor assembly along a first recess of the I-beam, determining changes in a spacing between the first upper block and the first lower block based on a first wear signal from the first pressure sensor as the sensor assembly traverses along the I-beam, and identifying worn areas of the I-beam based on the changes in the spacing between the first upper block and the first lower block.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
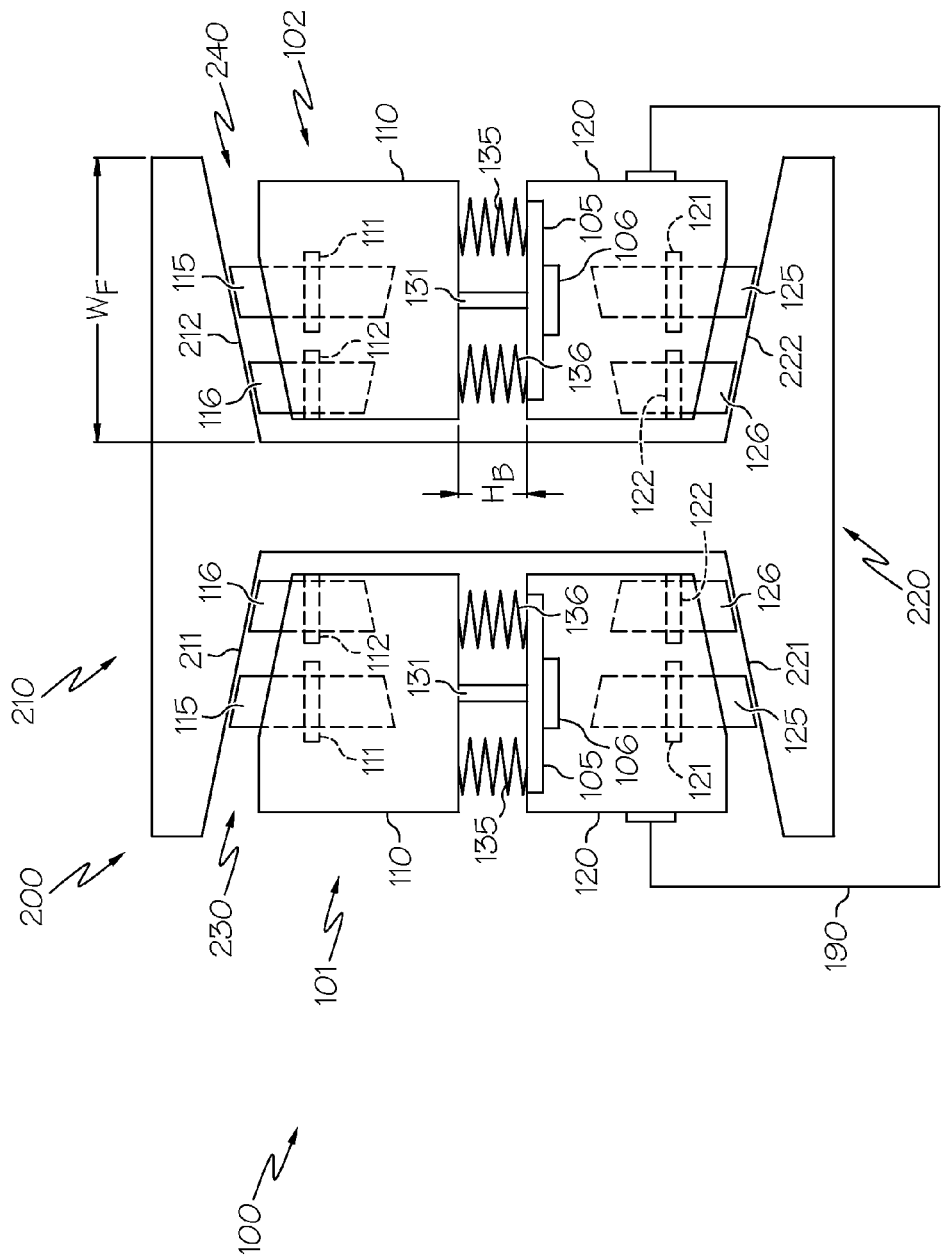
FIG. 1 depicts an I-beam wear assessment trolley on an I-beam according to one or more embodiments shown and described herein.

FIG. 1 generally depicts one embodiment of an I-beam wear assessment trolley for continuously monitoring flange wear along an I-beam. The I-beam wear assessment trolley generally comprises a first sensor assembly and a second sensor assembly. Both the first and second sensor assemblies comprise at least one biasing member to force the upper and lower blocks to expand and contract against the upper and lower flanges of the I-beam as the I-beam wear assessment trolley travels along the I-beam. Pressure sensors measure the pressure as the upper and lower portions of the blocks expand and contract to compensate for flange wear. The measurement of pressure can thereby be utilized to identify potentially worn portions of the I-beam to allow for repair or replacement. Various embodiments of the I-beam wear assessment trolley and the operation of the I-beam wear assessment trolley will be described in more detail herein.

Referring now to FIG. 1, an exemplary I-beam wear assessment trolley 100 is illustrated in connection with an I-beam 200. The I-beam 200 generally comprises an upper flange 210 connected to a lower flange 220 by a center web 201 to form an "I" shaped profile as illustrated in FIG. 1. The upper flange 210 can comprise a first upper flange half 211 and a second upper flange half 212 and the lower flange 220 member may similarly comprise a first lower flange half 221 and a second lower flange half 222. Each of the flanges of the I-beam 200 (i.e., the first upper flange half 211, the second upper flange half 212, the first lower flange half 221 and the second lower flange half 222) has a flange width $W_F$ corresponding to the length of the flange from the center web 201 to the edge of the flange. Furthermore, in some embodiments, the I-beam may comprise tapered flanges where each flange (i.e., the first upper flange half 211, the second upper flange half 212, the first lower flange half 221 and the second lower flange half 222) tapers from the center web 201 to the edge of the flange, as illustrated in FIG. 1. Furthermore, the upper flange 210, the lower flange 220 and the center web 201 of the I-beam 200 combine to form a first recess 230 and a second recess 240 in which the I-beam wear assessment trolley 100 may be positioned. As used herein, first refers to the first side of the profile of the I-beam 200, or the side containing the first recess 230 as indicated on the profile of the I-beam 200 in FIG. 1, and second refers to the second side of the profile of the I-beam 200, or the side containing the second recess 240 as indicted on the profile of the I-beam 200 in FIG. 1.

In the embodiment shown in FIG. 1, the I-beam wear assessment trolley 100 may generally comprise a first sensor assembly 101 and a second sensor assembly 102 connected to the first sensor assembly 101 by a coupling yoke 190. In the embodiment described herein, the first sensor assembly 101 and the second sensor assembly 102 are mirror of mages of another. Accordingly, the I-beam wear assessment trolley 100 will be described herein with specific reference to the first sensor assembly 101 with the understanding that the second assembly 102 has a similar construction.

The first sensor assembly 101 may generally comprise a first upper block 110 and a first lower block 120 operable to be disposed and ride within the first recess 230 of an I-beam 200. The first upper block 110 may comprise at least one first upper roller element designed to facilitate traversing (e.g. rolling) the first sensor assembly between the flanges of the I-beam 200. The at least one first upper roller element can comprise wheels, balls, tracks, rollers or any other suitable device for riding along the first upper flange half 211 of the I-beam 200. For example, as illustrated in FIG. 1, the at least one first upper roller element of the first upper block 110 comprises a first upper outer wheel 115 and a first upper inner wheel 116 adjacent to the first upper outer wheel 115. In one embodiment, where the flanges of the I-beam are tapered, the first upper outer wheel 115 and the first upper inner wheel 116 may also be tapered to correspond to the types of the flanges. In one embodiment, the first upper outer wheel 115 and/or the first upper inner wheel 116 can comprise a steel or similar alloy that resists wear upon travel. Alternatively, the first upper outer wheel 115 and/or the first upper inner wheel 116 can comprise any alternative composite durable material. In yet another embodiment, the first upper outer wheel 115 and the first upper inner wheel 116 can comprise any other material suitable for traversing the surface of the I-beam 200. However, it should be understood that the wheels may be constructed of any suitable material which is wear resistant.

Figure 4:
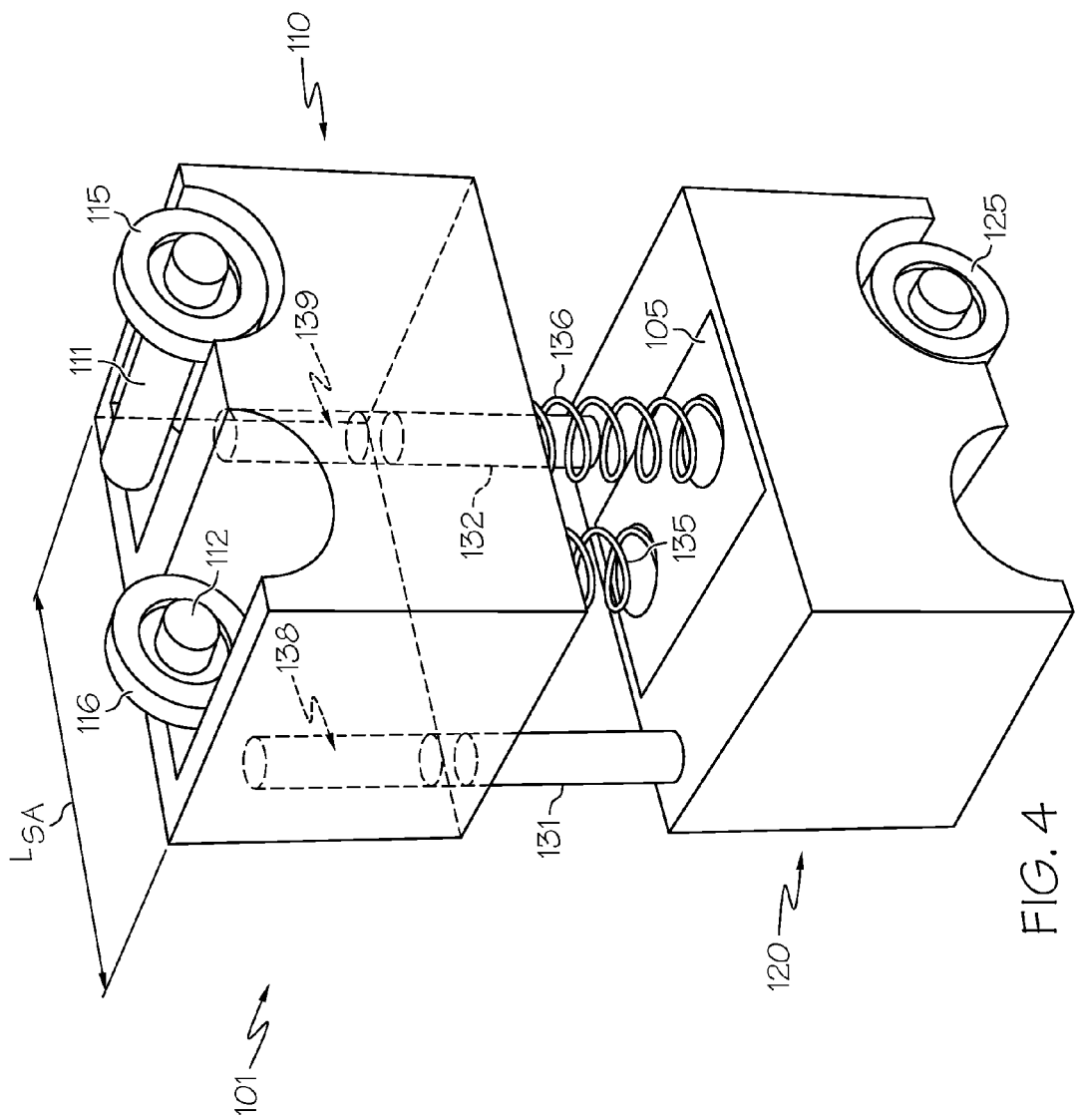
FIG. 4 depicts a first sensor assembly of an I-beam wear assessment trolley according to one or more embodiments shown and described herein.

Referring to FIGS. 1 and 4, in an exemplary embodiment, the first upper outer wheel 115 and the first upper inner wheel 116 may be connected to the first upper block 110 by one or more axles 111, 112, respectively. Furthermore, the first upper outer wheel 115 and the first upper inner wheel 116 may be spaced apart in the flange width $W_F$ direction so that the first upper outer wheel 115 and the first upper inner wheel 116 traverse along the first upper flange half 211 on different pathways. Such an embodiment may allow for broader tracking of wear along the flange width $W_F$ of the first upper flange half 211 by allowing the first upper outer wheel 115 and the first upper inner wheel 116 to follow different contours on the flange. The first upper outer wheel 115 and the first upper inner wheel 116 may also be staggered along the sensor assembly length $L_{SA}$ of the first sensor assembly 101 so that the first sensor assembly does not tip forwards or backwards when riding along the I-beam 200. In another embodiment, the first upper block 110 may comprise alternative first upper roller element configurations or embodiments. For example, in one embodiment, the first upper block 110 may comprise a single first upper wheel or three or more first upper wheels. In an alternative embodiment, the roller elements may comprise ball bearings or rotating tracks. In yet another alternative embodiment, the first upper block 110 may be constructed without roller elements. For example, the surface of the first upper block 110 and the surface of the first upper flange half 211 may each comprise smooth surfaces that provide minimal friction there between such that the first upper block 110 can traverse over the first upper flange half 211 without the assistance of first upper roller elements like the first upper outer wheel 115 and the first upper inner wheel 116.

Still referring to FIG. 1, the first sensor assembly 101 of the I-beam assessment trolley 100 further comprises a first lower block 120 similar to the first upper block 110. The first lower block 120 may be constructed in a similar manner as the first upper block 110. For example, the first lower block 120 may comprise at least one first lower roller element designed to facilitate traversing (e.g. rolling) the first sensor assembly between the flanges of the I-beam 200. The at least one first lower roller element can comprise wheels, balls, tracks, rollers or any other suitable device for riding along the first lower flange half 221 of the I-beam 200. For example, as illustrated in FIG. 1, the at least one first lower roller element of the first lower block 120 comprises a first lower outer wheel 125 and a first lower inner wheel 126 adjacent to the first lower outer wheel 125. In one embodiment, where the flanges of the I-beam 200 are tapered, the first lower outer wheel 125 and the first lower inner wheel 126 may also be tapered to correspond to the types of the flanges. In another embodiment, the first lower outer wheel 125 and/or the first lower inner wheel 126 can comprise a steel or similar alloy that resists wear upon travel. Alternatively, the first lower outer wheel 125 and/or the first lower inner wheel 126 can comprise any alternative composite durable material. In yet another embodiment, the first lower outer wheel 125 and the first lower inner wheel 126 can comprise any other material suitable for traversing the surface of the I-beam 200. However, it should be understood that the wheels may be constructed of any suitable material which is wear resistant.

Referring to FIGS. 1-4, in an exemplary embodiment, the first lower outer wheel 125 and the first lower inner wheel 126 may be connected to the first lower block 120 by one or more axles 121. Furthermore, the first lower outer wheel 125 and the first lower inner wheel 126 may be spaced apart in the flange width $W_F$ direction so that the first lower outer wheel 125 and the first lower inner wheel 126 traverse along the first lower flange half 221 on different pathways. Such an embodiment may allow for broader tracking of wear along the flange width $W_F$ of the first lower flange half 221 by allowing the first lower outer wheel 125 and the first lower inner wheel 126 to follow different contours on the flange. The first lower outer wheel 125 and the first lower inner wheel 126 may also be staggered along the sensor assembly length $L_{SA}$ of the first sensor assembly 101 so that the first sensor assembly does not tip forwards or backwards when riding along the I-beam 200. In another embodiment, the first lower block 120 may comprise alternative first lower roller element configurations or embodiments. For example, in one embodiment, the first lower block 120 may comprise a single first lower wheel or three or more first lower wheels. In an alternative embodiment, the roller elements may comprise ball bearings or rotating tracks. In yet another alternative embodiment, the first lower block 120 may be constructed without roller elements. For example, the surface of the first lower block 120 and the surface of the first lower flange half 221 may each comprise smooth surfaces that provide minimal friction there between such that the first lower block 120 can traverse over the first lower flange half 221 without the assistance of first lower roller elements like the first lower outer wheel 125 and the first lower inner wheel 126.

The first sensor assembly 101 further comprises at least one biasing member positioned between the first upper block 110 and the first lower block 120 which biases the first upper block and the first lower block of the first sensor assembly away from one another such that the first sensor assembly 101 expands and contracts between the first upper flange half 211 and the first lower flange half 221. For example, the biasing member may include springs, pneumatic cylinders or any other device operable to exert a biasing force against the first upper block 110 and the first lower block 120. For example, referring to FIGS. 1-4, in one exemplary embodiment, the first upper block 110 and the first lower block 120 may be biased away from one another by one or more springs 135, 136. The one or more springs 135, 136 may be positioned between the first upper block 110 and the first lower block 120 such that they are exert a biasing force to force the first upper block 110 to ride along the first upper flange half 211 of the I-beam 200 and force the first lower block 120 to ride along the first lower flange half 221 of the I-beam 200. By exerting a biasing force, the one or more springs 135, 136 separate the first upper block 110 and the first lower block 120 by a block spacing $H_B$. The block spacing $H_B$ for the first sensor assembly 101 will change based on the distance between the first upper flange half 211 and the first lower flange half 221. Specifically, where a portion of the first upper flange half 211 or the first lower flange half 221 is relatively worn (i.e., the flange is relatively thinner because less material is present), the distance between the first upper flange half 211 and the first lower flange half 221 will increase causing the springs to expand and the block spacing $H_B$ for the first sensor assembly 101 to increase. The one or more springs 135, 136 may be connected to the first upper block 110 and the first lower block 120 via any connection suitable to maintain the springs between the first upper block 110 and the first lower block 120 while the springs exert a biasing pressure on the first upper block 110 and the first lower block 120. For example the one or more first springs 135, 136 may be connected to the first upper block 110 and the first lower block 120 by positioning the springs in seats formed in the first upper block 110 and the first lower block 120. Alternatively, the one or more springs 135, 136 may be connected to the first upper block 110 and the first lower block 120 through welds, brackets, screws, bolts or any other operable connection, or combinations thereof.

In one embodiment, such as that illustrated in FIG. 1, the one or more first springs may comprise a first outer spring 135 and a first inner spring 136. The first outer spring 135 may be disposed between the first upper block 110 and the first lower block 120 at a distance farther from the center web 201 of the I-beam 200 than the distance of the first inner spring 136 from the center web 201 of the I-beam 200. In another embodiment, the first outer spring 135 and the first inner spring 136 may be aligned with the first upper wheels and the first lower wheels. For example, the first outer spring 135 may be vertically aligned with the first upper outer wheel 115 and the first lower outer wheel 125 while the first inner spring 136 may be vertically aligned with the first upper inner wheel 116 and the first lower inner wheel 126.

Figure 3:
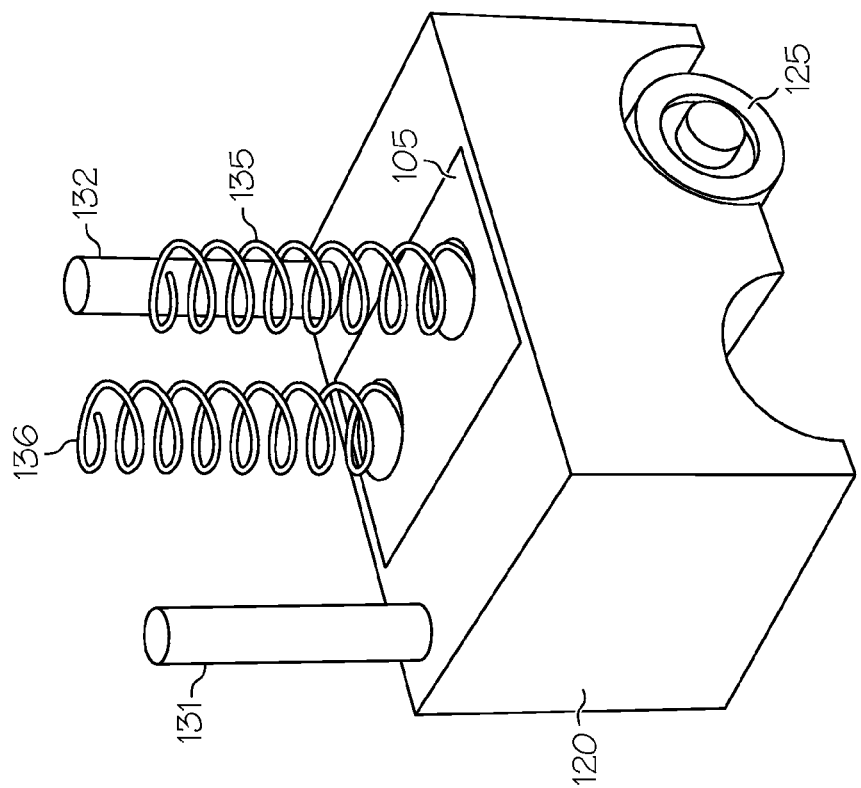
FIG. 3 depicts a lower block of a first sensor assembly of an I-beam wear assessment trolley according to one or more embodiments shown and described herein.

The first sensor assembly 101 further comprises a first pressure sensor 106 operable to measure the force exerted on the first upper block 110 and the first lower block 120. The first pressure sensor 106 can comprise any device or sensor operable to detect pressure from the at least one first biasing member. For example, the first pressure sensor 106 can comprise pressure paper, a load cell, a piezoelectric material, or any other similar device. In one particular example, the first pressure sensor 106 may comprise a FlexiForce Force Sensor available from Tekscan. The first pressure sensor 106 is disposed between the first upper block 110 or the first lower block 120 so that it is operable to measure the pressure from the force exerted on the first lower block 120 and the first upper block 110. In one embodiment, such as that illustrated in FIG. 1, a first spring plate 105 may separate the first springs from the first pressure sensor 106. The first spring plate 105 may allow for the pressure from each individual first spring to be transferred and distributed over to the first pressure sensor 106 such that a single first pressure sensor 106 can measure the change in pressure from a plurality of first springs. For example, where the first sensor assembly 101 comprises a first outer spring 135 and a first inner spring 136, such as illustrated in FIG. 1, the bottom ends of the first outer spring 135 and the first inner spring 136 may be secured to the first spring plate 105, and the upper ends of the first outer spring 135 and the first inner spring 136 may be secured to the first upper block 110. The first pressure sensor 106 may be disposed between the first spring plate 105 and the first lower block 120 so that the pressure from the first outer spring 135 and the first inner spring 136 may be jointly passed through the first spring plate 105 to the first pressure sensor 106. In another embodiment, the first pressure sensor 106 and the first spring plate 105 may reside in a first pocket 107 formed in either the first upper block 110 or the first lower block 120. For example, in the embodiment shown in FIGS. 1-4, the first pocket 107 is formed in the first lower block 120. The first spring plate 105 and the first pressure sensor 106 may thereby be disposed in the first pocket 107 such that the first spring plate 105 becomes substantially flush with the surface of the first lower block 120 as seen in FIG. 3. In yet another embodiment (not shown), an elastically deformable and recoverable material such as a rubber pad or any other intermediary material may be disposed between the first spring plate 105 and the first pressure sensor 106 to provide for uniform distribution of the biasing force onto the first pressure sensor 106.

Using the first inner spring 136 and the first outer spring 135 in conjunction with the first pressure sensor 106 allows the force exerted on the first upper block 110 and the first lower block 120 to be registered by the first pressure sensor 106 which, in turn, outputs an electrical signal indicative of the force (i.e., a first wear signal). Because the first outer spring 135 and the first inner spring 136 have a known spring constant "k", and because the electrical signal emitted from the first pressure sensor 106 is indicative of the force F exerted on the springs, the displacement of the springs (and therefore the change in the spacing $H_B$ between the first upper block 110 and the first lower block 120) can be determined by the relationship F=k·x, where x=$H_B$ and thus $H_B$=F/k. Accordingly, when wear is present on the flanges, the value of the $H_B$ increases while, when no wear is present, the value of the $H_B$ remains substantially uniform over the length of the I-Beam.

In addition, the first upper block 110 may be vertically aligned with the first lower block 120. Specifically, the first upper block 110 and the first lower block 120 may be aligned with one or more first guide posts 131, 132. For example, as illustrated in FIGS. 1-4, a first front guide post 131 may be received by guide bores within both the first upper block 110 and the first lower block 120. Likewise, a first rear guide post 132 may also be received by its own guide bores within both the first upper block 110 and the first lower block 120. The first front guide post 131 and the first rear guide post 132 may thereby physically align the first upper block 110 with the first lower block 120 such that the two blocks do not shift along the flange width $W_F$ direction relative the other. In one embodiment, the first front guide post 131 and the first rear guide post 132 may be received within the guide bores with no physical attachment to the first upper block 110 or the first lower block 120. In another embodiment, the first front guide post 131 and the first rear guide post 132 may be physically attached to either the first upper block 110 or the first lower block 120 either within the guide bore or directly to the surface. It should be appreciated that any other interaction between the first front guide post 131, the first rear guide post 132, the first upper block 110 and the first lower block 120 may be realized so long as the first upper block 110 and the first lower block 120 can move vertically relative the other such that the block height $H_B$ may change with flange wear.

While specific reference has been made to an I-beam wear assessment trolley 100 comprising a first sensor assembly 101, in one exemplary embodiment the I-beam wear assessment trolley 100 may further comprise a second sensor assembly 102 to ride in the second cavity 240 of the I-beam 200. As illustrated in FIG. 1, in such an embodiment, the second sensor assembly 102 is a mirror image of the first sensor assembly 101. Specifically, the second sensor assembly 102 can similarly comprise a second upper block 110 and a second lower block 120 biased by a second outer spring 135 and a second inner spring 136. The second upper block 102 of the second sensor assembly 102 can comprise a second upper outer wheel 115 and a second upper inner wheel 116 while the second lower block 120 of the second sensor assembly 102 can comprise a second lower outer wheel 125 and a second lower inner wheel 126. The second sensor assembly 102 can comprise any other embodiments that either mirrors the first sensor assembly 101 or otherwise allows for the measuring of flange wear in the second cavity 240 of the I-beam 200 while the first sensor assembly 101 measures flange wear in the first cavity 230 of the I-beam 200.

Referring now to FIG. 1, where the I-beam wear assessment trolley 100 comprises both a first sensor assembly 101 and a second sensor assembly 102, the first sensor assembly 101 and the second sensor assembly 102 may be connected by a coupling yoke 190. The coupling yoke 190 can comprise any device operable to physically connect the first sensor assembly 101 to the second sensor assembly 102 allowing the first sensor assembly 101 and the second sensor assembly 102 to traverse the I-beam 200 together. In one embodiment, such as that illustrated in FIG. 1, the coupling yoke 190 may comprise a rigid material operable to connect to the first lower block 120 of the first sensor assembly 101, extend down and around the lower flange 220 of the I-beam 200, and connect to the second lower block 120 of the second sensor assembly 102. In an alternative embodiment, the coupling yoke 190 may connect to the first upper block 110 of the first sensor assembly 101, extend up and over the upper flange 210 of the I-beam 200 and connect to the second upper block 110 of the second sensor assembly 102. In yet another embodiment, the I-beam wear assessment trolley 100 may comprise a plurality of coupling yokes 190 operable to physically connect the first sensor assembly 101 to the second sensor assembly 102. In yet another embodiment, the coupling yoke 190 may be detachable from the first sensor assembly 101 and/or the second sensor assembly 102 to assist in loading or unloading the I-beam wear assessment trolley 100 onto or off of the I-beam 200. It should be appreciated that the I-beam wear assessment trolley 100 may comprise any other alternative or additional coupling yoke 190 operable to physically connect the first sensor assembly 101 to the second sensor assembly 102 allowing the first sensor assembly 101 and the second sensor assembly 102 to traverse along the I-beam 200 together.

Figure 5:
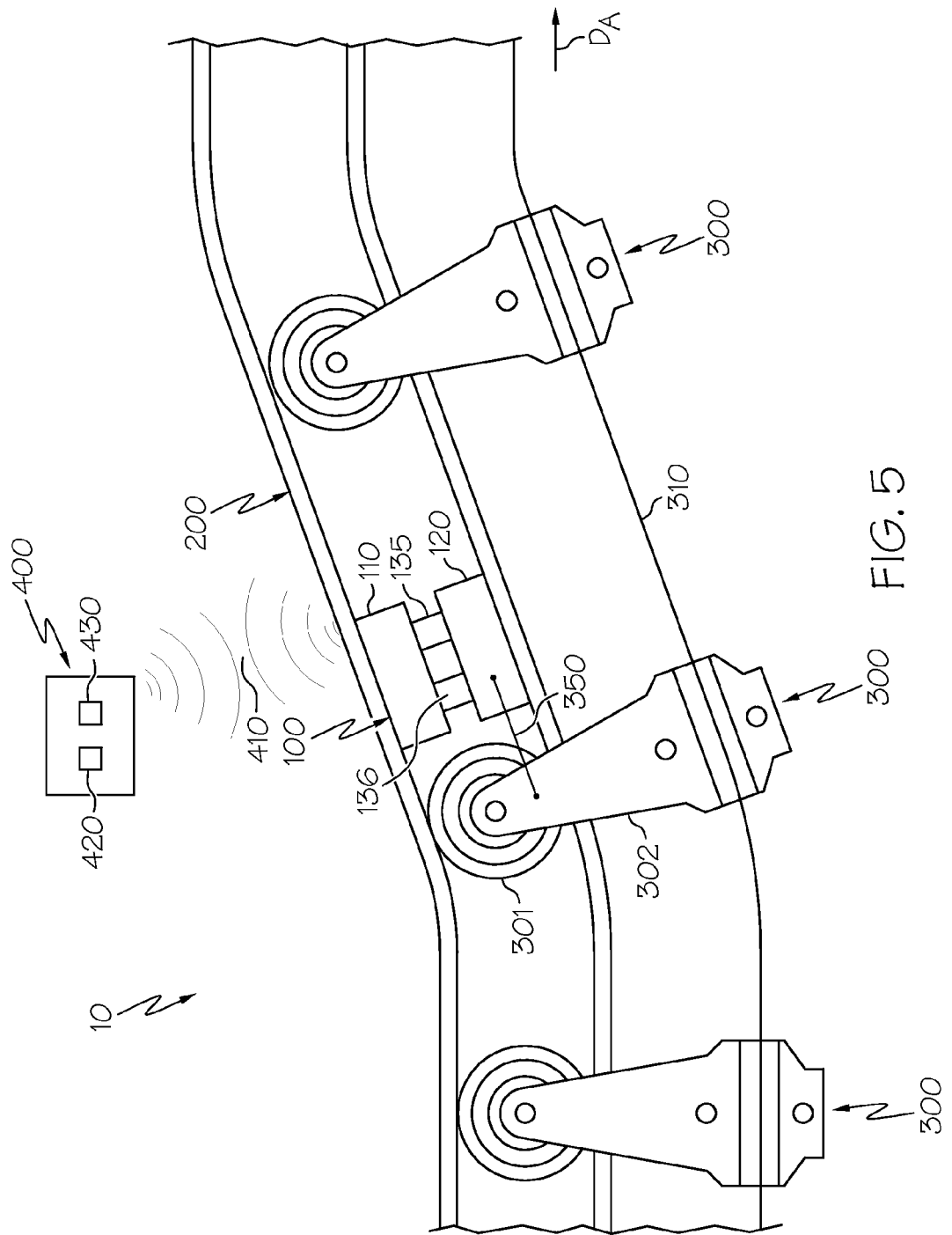
FIG. 5 depicts an I-beam wear assessment trolley positioned in an I-beam according to one or more embodiments shown and described herein.

Referring now to FIG. 5, the I-beam wear assessment trolley is communicatively coupled to a computer 400. As used herein, "communicatively coupled" means operable to send wear signals (i.e., pressure readings) from the pressure sensors 106 to the computer 400 via wired or wireless communication 410. The computer 400 can comprise any type of computer, storage medium or other device operable to receive and store the pressure readings from the first pressure sensor 106. For example, in one embodiment, the computer 400 may comprise a processor 420 and a memory 430 with computer readable and executable instructions. In such an embodiment, the processor 420 can execute the computer readable and executable instructions to, for example, receive a first wear signal from the first pressure sensor indicative of the spacing between the first upper block 110 and the first lower block 120 and store the first wear signal in the memory based on the position of the I-beam wear assessment trolley 100 along the length of an I-beam 200. In another embodiment, such as where the I-beam wear assessment trolley 100 further comprises a second sensor assembly, the processor 420 may further be able to execute the computer readable and executable instructions to receive a second wear signal from a second pressure sensor indicative of the spacing between the second upper block and the second lower block and store the second wear signal in the memory based on the position of the I-beam wear assessment trolley 100 along the length of the I-beam 200.

Figure 2:
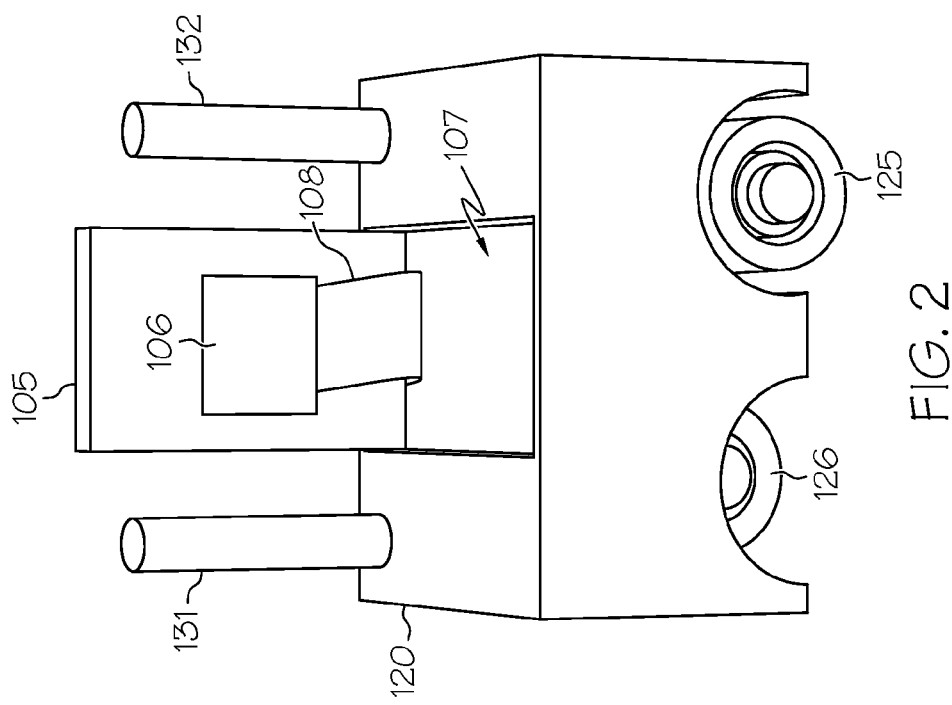
FIG. 2 depicts a lower block of a first sensor assembly of an I-beam wear assessment trolley according to one or more embodiments shown and described herein.

In one embodiment, the I-beam wear assessment trolley 100 may itself comprise the computer 400. In such an embodiment, the pressure sensors 106 can communicate the wear signals to the computer 400 via a communication line 108 such as illustrated in FIG. 2. In another embodiment, the computer 400 may be separate from the I-beam wear assessment trolley 100 such as illustrated in FIG. 5. In such an embodiment, the pressure sensors 106 may communicate wirelessly 410 with the computer 400. Any alternative computer 400 configuration may alternatively or additionally be incorporated such that the measured pressure from the pressure sensors 106 may be recorded and analyzed.

It should be understood that the pressure sensors may be used to determine the pressure applied from the force of the biasing member on the I-beam wear assessment trolley 100. Where the pressure in the sensor assemblies 101, 102 is derived from springs as discussed above, springs may be selected based on the block height $H_B$ of the sensor assemblies 101 as well as the sensitivity of the pressure sensors 106. For example, the springs may comprise a relatively high spring constant (requiring greater force to change the length of the spring) when being used in conjunction with a relatively sensitive pressure sensors 106. Conversely, the springs may comprise a relatively low spring constant (requiring less force to change the length of the spring) when being used in conjunction with a relatively less sensitive pressure sensors 106. It should be appreciated that any other spring or pressure sensor parameter may further be adjusted to record the first pressure wear signal and the second pressure wear signal in the first sensor assembly 101 and the second sensor assembly 102 as they expand or contract with the worn portions of the I-beam 200.

Referring now to FIG. 5, an I-beam rail guide system 10 is illustrated in which the I-beam wear assessment trolley 100 is connected to a carrier assembly 300 which is coupled to the I-beam 200. The carrier assembly 300 can comprise any apparatus used to pick-up, drop-off, transport and/or otherwise assist in the construction, repair or modification of an article of manufacture. Articles of manufacture can comprise any type of good that may be used in a manufacturing systems such as automotive or machined parts, consumer goods, or any other tangible apparatus. For example, as illustrated in FIG. 5, the carrier assembly 300 may comprise a carrier wheel 301 operable to traverse the I-beam 200. A carrier arm 302 may be connected to the carrier wheel 301 wherein the carrier arm 302 may be operable to assist in the transport of the article of manufacture. The carrier assembly 300 traverses along the I-beam 200 in direction of assembly $D_A$ between assembly work stations or to other target locations. The carrier assembly 300 may be self powered with an on-board motor or engine, powered by an external motor or engine, powered by a carrier chain 320 connecting a plurality of carrier assemblies 300 (as illustrated in FIG. 5) or, alternatively or additional, powered by any other operable mechanism.

In one embodiment shown in FIG. 5, the I-beam wear assessment trolley 100 is connected to the carrier assembly 300 with a carrier connection arm 350 such that the carrier assembly 300 and the I-beam wear assessment trolley 100 traverse along the I-beam together in the direction of assembly $D_A$. In one embodiment, illustrated in FIG. 5, the carrier connection arm 350 may comprise a rigid arm fixedly connecting the I-beam wear assessment trolley 100 to the carrier assembly 300. In such an embodiment, the carrier connection arm can push the I-beam wear assessment trolley 100 when in front of the carrier assembly 300 or can pull the I-beam wear assessment trolley 100 behind the carrier assembly 300. In another embodiment, the carrier connection arm 350 may comprise a rope, tie wrap or other flexible device operable to pull the I-beam wear assessment trolley 100 when behind the carrier assembly 300. It should be appreciated that any other alternative carrier connection arm 350 may additionally or alternatively be used such that the carrier assembly 300 and the I-beam wear assessment trolley 100 traverse along the I-beam together.

Figure 6:
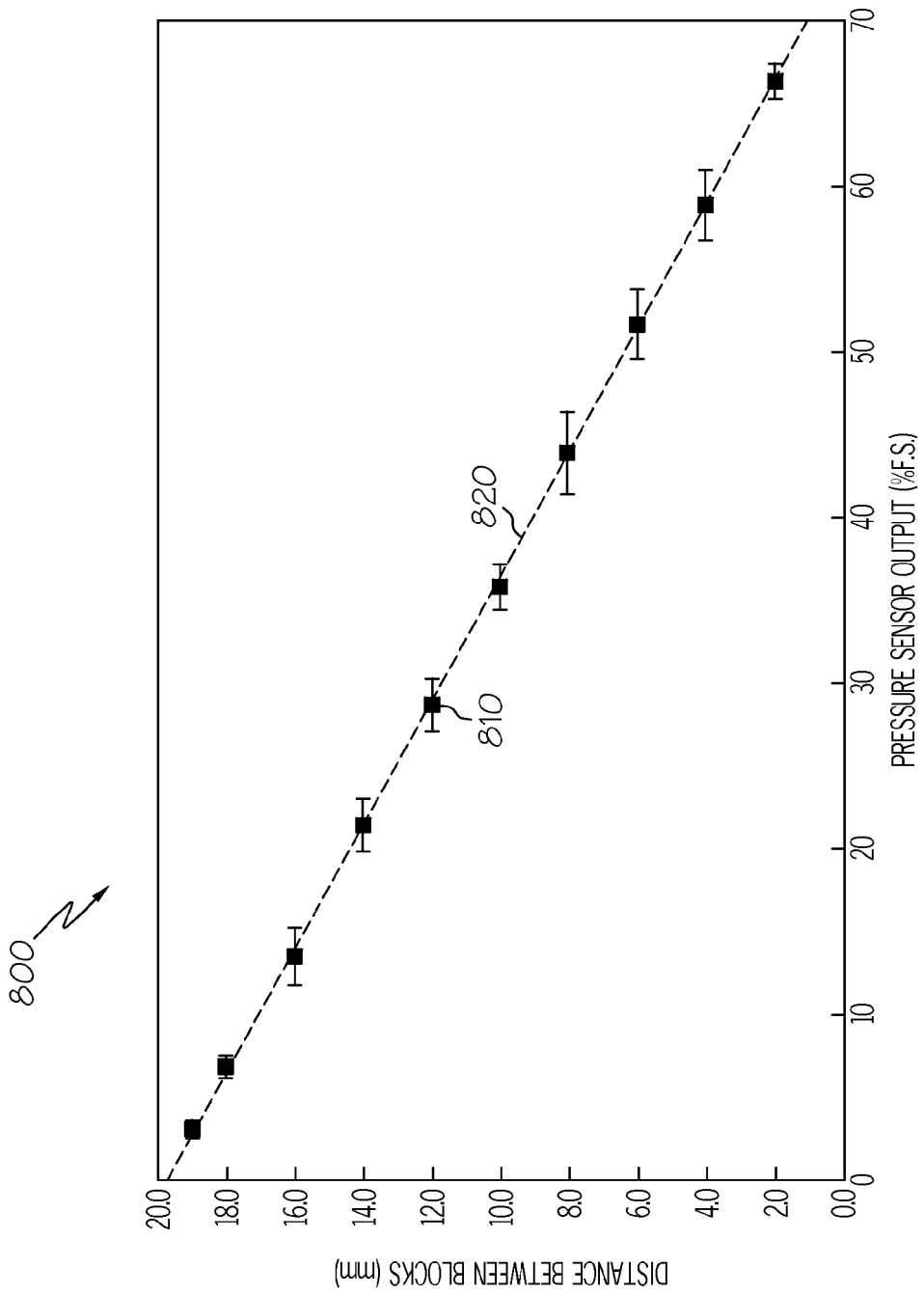
FIG. 6 depicts an exemplary calibration graph for an I-beam wear assessment trolley according to one or more embodiments shown and described herein.

Referring now to FIGS. 1-5, the I-beam wear assessment trolley 100 may traverse the I-beam 200 to measure the wear on the I-beam flanges. Specifically, in one embodiment, the I-beam wear assessment trolley 100 may be calibrated to associate the wear signals from the pressure sensors with a block height $H_B$, which in turn represents the amount of wear of the I-beam 200. For example, the first sensor assembly 101 or the second sensor assembly 102 of the I-beam wear assessment trolley 100 may be subjected to calibration. In such an embodiment, a controllable vice may compress the first upper block 110 and the first lower block 120 of the first sensor assembly 101 similar to how the first upper flange half 211 and the first lower flange half 221 would on the first sensor assembly 101. The controllable vice may first apply no pressure about the first sensor assembly 101 such that the at least one biasing member expands fully. Then the controllable vice is then used to compress the first sensor assembly 101 while the first pressure sensor 106 measures an increase in pressure from compressing the at least one first biasing member due to the decreasing block height $H_B$ of the first sensor assembly 101. Referring to FIG. 6, a calibration graph is illustrated plotting the calibration data. Specifically the calibration graph 800 plots a plurality of data points 810 comprising the pressure sensor output (i.e., the wear signals) in terms of percent force sensing (% F.S.) against the distance between the blocks (i.e., the block height $H_B$). Furthermore, a linear fit line 820 may be derived to extrapolate the distance between the blocks for a wider range of pressure sensor output percentages. An operator may thereby use the first wear signals from the first pressure sensor 106 to determine the distance between the blocks which, in turn, demonstrates the amount of wear on the I-beam. For example, lower pressure sensor outputs indicate greater distance between blocks which results from increased wear of the I-beam 200 causing the first upper block 110 and first lower block 120 to expand away from one another.

Figure 7:
FIG. 7 depicts a plot of time (x-axis) vs. pressure sensor output (y-axis) from an I-beam wear assessment trolley according to one or more embodiments shown and described herein.

In operation, the wear signals from the first pressures can be used to identify worn portions of the I-beam 200 needing or potentially needing repair or replacement. For example, referring to the first sensor assembly 101, as the I-beam wear assessment trolley 100 traverses the length of the I-beam 200, variations in the thickness of the I-beam flanges cause the upper block 101 and the lower block 102 of the first sensor assembly 101 to move towards or away from one another due to the biasing members 135, 136 disposed there between. Changes in the relative block height $H_B$ between the upper block 110 and the lower block 120 are indicative of the wear of the I-beam flanges which, in turn, are registered by the pressure sensor 106 which output an electrical signal corresponding to the amount of wear of the I-Beam to the computer 400. Furthermore, the pressure measured from the pressure sensors 106 may be correlated with the location on the I-beam 120 in which the pressure was ascertained. For example, in one embodiment, the I-beam wear assessment trolley 100 may traverse along an I-beam loop of a set length at a constant speed. As illustrated in FIG. 7, the pressure data 910 from the first pressure sensor 106 may be plotted against the time in which the first wear signal was ascertained. By knowing the time it takes for the I-bream wear assessment trolley 100 to traverse the I-beam 200, low pressure indicating worn I-beam positions may be identified to specific I-beam locations. In another embodiment, the I-beam wear assessment trolley 100 may comprise a tracker device that can report or record the specific location of the I-beam wear assessment trolley 100 along the I-beam 200 to the computer 400 along with the wear signals. For example, the tracker device may comprise a GPS unit or an RFID tag that is repeatedly scanned and registered along the length of the length of the I-beam 200. Thus, the relevant portion of the I-beam 200 may then be inspected, repaired or replaced depending on the amount of wear.

In another embodiment, as illustrated in FIG. 7 the computer 400 may compare a warning threshold 920 to the wear signals 910 on the I-beam assessment graph 900 to alert an operator when the wear signals are low enough to indicate potentially dangerous wear of the I-beam 200. In such an embodiment, the signals from the pressure sensors may be analyzed in real-time by the computer 400 as the data is collected, or in the alternative, the signals from the pressure sensors may be analyzed periodically after a complete set of wear signals 910 is ascertained by the computer 400 corresponding to the entire length of the I-beam. In another embodiment, the I-beam wear assessment trolley 100 may comprise a wear indicator operable to mark the portion of the I-beam determined by the pressure sensors to have wear exceeding a predetermined threshold. Specifically, the I-beam wear assessment trolley 100 may continuously measure the first pressure sensor or the second pressure sensor and, when the wear signal 910 of the first pressure sensor or the second pressure sensor reaches a warning threshold 920, the computer can activate the wear indicator to mark or identify the location of the I-beam 200 with the wear. For example, in such an embodiment, the wear indicator can comprise a paint gun operable to spray the I-beam where there is wear, a horn that is triggered when it passes over a worn section, a light that illuminates when it passes over a worn section, or any other alternative apparatus that indicates the location of wear on the I-beam 200.

It should now be appreciated that I-beam wear assessment trolleys may be utilized to automatically measure the wear of an I-beam. Biasing the I-beam wear assessment trolley can force upper blocks and lower blocks to expand and contract continuously so that they ride against the adjacent flange of the I-beam. A pressure sensor can further measure the pressure in the springs caused by the expansion and contraction of the upper blocks and the lower blocks and correlate these wear signals to wear along the flanges of the I-beam. In addition, the I-beam wear assessment may be connected to a carrier assembly to automatically traverse along the I-beam while continuously measuring the wear. The first wear signal or second wear signal (indicating the amount of wear of the I-beam) can be correlated to the location on the I-beam in which the pressure was ascertained so that worn sections of the I-beam may be repaired or replaced.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An I-beam wear assessment trolley comprising:
a first sensor assembly comprising:
a first upper block;
a first lower block aligned vertically with the first upper block such that a lower face of the first upper block faces an upper face of the first lower block;
a first pressure sensor positioned between the first upper block and the first lower block; and
at least one first biasing member comprising a first inner spring positioned between the first pressure sensor and the lower face of the first upper block and the upper face of the first lower block of the first sensor assembly, wherein the at least one first biasing member biases the first upper block and the first lower block of the first sensor assembly away from one another.

2. The I-beam wear assessment trolley of claim 1 further comprising:
a second sensor assembly removably coupled to the first sensor assembly with a coupling yoke, the second sensor assembly comprising:
a second upper block;
a second lower block;
a second pressure sensor positioned between the second upper block and the second lower block; and
at least one second biasing member positioned between the second pressure sensor and either the second upper block or the second lower block of the second sensor assembly, wherein the second biasing member biases the second upper block and the second lower block of the second sensor assembly away from one another.

3. The I-beam wear assessment trolley of claim 1 wherein the at least one first biasing member comprises the first inner spring and a first outer spring.

4. The I-beam wear assessment trolley of claim 1 wherein:
the first pressure sensor is positioned in a first pocket in the first lower block;
a first spring plate is positioned in the first pocket such that the first pressure sensor is positioned between the first pocket and the first spring plate; and
the at least one first biasing member is coupled to the first spring plate.

5. The I-beam wear assessment trolley of claim 4 further comprising an elastically deformable and recoverable material positioned between the first pressure sensor and the first spring plate.

6. The I-beam wear assessment trolley of claim 1 wherein the first lower block and the first upper block each comprise at least one roller element to facilitate rolling the first sensor assembly between flanges of an I-beam.

7. The I-beam wear assessment trolley of claim 6 wherein the at least one roller element of each of the first lower block and the first upper block is at least one wheel.

8. The I-beam wear assessment trolley of claim 7 wherein the at least one wheel is tapered to correspond to a taper of a flanged portion of the I-beam.

9. An I-beam wear assessment trolley comprising:
a first sensor assembly comprising:
a first upper block;
a first lower block aligned vertically with the first upper block such that a lower face of the first upper block faces an upper face of the first lower block;
a first pressure sensor positioned between the first upper block and the first lower block; and
at least one first biasing member comprising a first inner spring positioned between the first pressure sensor and the lower face of the first upper block and the upper face of the first lower block of the first sensor assembly, wherein the at least one first biasing member biases the first upper block and the first lower block of the first sensor assembly away from one another; and a second sensor assembly removably coupled to the first sensor assembly with a coupling yoke, the second sensor assembly comprising:
a second upper block;
a second lower block;
a second pressure sensor positioned between the second upper block and the second lower block; and
at least one second biasing member positioned between the second pressure sensor and either the second upper block or the second lower block of the second sensor assembly, wherein the second biasing member biases the second upper block and the second lower block of the second sensor assembly away from one another; and a computer communicatively coupled to the first sensor assembly and the second sensor assembly, the computer comprising a processor and a memory with computer readable and executable instructions, wherein the processor executes the computer readable and executable instructions to:
receive a first wear signal from the first pressure sensor indicative of a first block height between the first upper block and the first lower block;
receive a second wear signal from the second pressure sensor indicative of a second block height between the second upper block and the second lower block; and
store the first wear signal and the second wear signal in the memory based on a position of the first sensor assembly and the second sensor assembly along a length of an I-beam.

10. The I-beam wear assessment trolley of claim 9 wherein the at least one first biasing member comprises the first inner spring and a first outer spring and the at least one second biasing member comprises a second inner spring and a second outer spring.

11. The I-beam wear assessment trolley of claim 9 wherein:
the first pressure sensor is positioned in a first pocket in the first lower block;
a first spring plate is positioned in the first pocket such that the first pressure sensor is positioned between the first pocket and the first spring plate;
the at least one first biasing member is coupled to the first spring plate,
the second pressure sensor is positioned in a second pocket in the second lower block;
a second spring plate is positioned in the second pocket such that the second pressure sensor is positioned between the second pocket and the second spring plate; and
the at least one second biasing member is coupled to the second spring plate.

12. The I-beam wear assessment trolley of claim 9 wherein:
the first lower block and the first upper block of the first sensor assembly each comprise at least one first roller element to facilitate rolling the first sensor assembly between flanges of the I-beam; and
the second lower block and the second upper block of the second sensor assembly each comprise at least one second roller element to facilitate rolling the second sensor assembly between the flanges of the I-beam.

13. The I-beam wear assessment trolley of claim 12 wherein the at least one first roller element of each of the first lower block and the first upper block and the at least one second roller element of each of the second lower block and the second upper block is at least one wheel.

14. The I-beam wear assessment system of claim 13 wherein the processor further executes the computer readable and executable instructions to compare the first wear signal and the second wear signal to a warning threshold.

15. The I-beam wear assessment system of claim 9 further comprising a carrier assembly connected to the first sensor assembly and/or the second sensor assembly.

16. The I-beam wear assessment system of claim 15 wherein the carrier assembly comprises:
a carrier wheel that rides along a first recess or a second recess of the I-beam; and
a carrier arm connected to the carrier wheel, wherein the carrier arm transports an article of manufacture.

17. The I-beam wear assessment system of claim 9 further comprising a wear indicator that indicates wear along the I-beam when the first wear signal from the first pressure sensor or the second wear signal from the second pressure sensor reaches a warning threshold.

18. A method for assessing the wear of an I-beam, the method comprising:
positioning a first sensor assembly between an upper flange and a lower flange of the I-beam, the first sensor assembly comprising a first upper block, a first lower block aligned vertically with the first upper block such that a lower face of the first upper block faces an upper face of the first lower block, a first pressure sensor positioned between the first upper block and the first lower block, and at least one first biasing member comprising a first inner spring positioned between the lower face of the first upper block and the upper face of the first lower block, wherein the at least one first biasing member biases the first upper block and the first lower block of the first sensor assembly away from one another;
traversing the first sensor assembly along a first recess of the I-beam;
determining changes in a spacing between the first upper block and the first lower block based on a first wear signal from the first pressure sensor as the sensor assembly traverses along the I-beam; and
identifying worn areas of the I-beam based on the changes in the spacing between the first upper block and the first lower block.

19. The method of claim 18 wherein the wherein the at least one first biasing member comprises the first inner spring and a first outer spring.

20. The method of claim 18 wherein the first lower block and the first upper block each comprise at least one roller element to facilitate traversing the first sensor assembly along the first recess of the I-beam.

* * * * *